United States Patent [19]

Satow

[11] Patent Number: 6,018,039

[45] Date of Patent: Jan. 25, 2000

[54] MC26 GENE EXPRESSION-REGULATORY REGION

[76] Inventor: Hiroyasu Satow, 9-1-803, Kami-Ikebukuro 4-chome, Toshima-ku, Tokyo 170, Japan

[21] Appl. No.: 08/688,376

[22] Filed: Jul. 30, 1996

[51] Int. Cl.[7] .......................... C07H 21/04; C07H 21/02; C12N 15/00

[52] U.S. Cl. ...................... 536/24.1; 536/23.1; 435/320.1

[58] Field of Search .................................. 536/23.1, 23.5, 536/24.1; 435/172.3, 320.1; 800/2, DIG. 4

[56] References Cited

FOREIGN PATENT DOCUMENTS 07194380  8/1995  Japan .

OTHER PUBLICATIONS

Nishimura, T. Direct submission to DDBJ. MPSRCH, pp. 1–4, Apr. 20, 1993.

Krimpenfort, et al. Generation of transgenic dairy cattle using 'in vitro' embryo production. Biotechnology, vol. 9, pp. 844–847, Sep. 1991.

Houdebine, L. M. Production of pharmaceutical proteins from transgenic animals. J. of Biotechnology, vol. 34, pp. 269–287, 1994.

Pursel et al. Genetic enginerring of Livestock. Science, vol. 244, pp. 1281–1288, Jun. 16, 1989.

Satow et al., "Post–Transcriptional Control of 26 K Casein Genes during Lactogenesis in Mouse Mammary Glands", J. Biochem. 99, vol. 99, No. 6, pp. 1639–1643 (1986).

Kawamura et al., "Modulation of the Transferred Mouse 26K Casein Gene in Mouse L Cells by Glucocorticoid Hormone", J. Biochem. 101, No. 1, pp. 103–110 (1987).

Nishimura et al., "Expression of the MC26 Gene Encoding GlyCAM–1 in the Lactating Mouse Mammary Gland", J. Biochem. vol. 114, No. 4, pp. 567–569 (1993).

Dowbenko et al., "Structure and Chromosonal Localization of the Murine Gene Encoding GLYCAM–1", The Journal of Biological Chemistry vol. 268, No. 6, pp. 4525–4529 (1993).

Dowbenko et al., "Glycosylation–dependent Cell Adhesion Molecular 1 (GlyCAM 1) Mucin Is Expressed by Lactating Mammary Gland Epithelial Cells and is Present in Milk", J. Clin. Invest. vol. 92, Aug. 1993, pp. 952–960.

Lasky et al., "An Endothelial Ligand for L–Selectin Is a Novel Mucin–like Molecule", Cell. vol. 69, Jun. 12, 1992, pp. 927–938.

Imai et al., "Sulphation requirement for GlyCAM–1, an endothelial ligand for L–selectin", Nature vol. 361, Feb. 11, 1993, pp. 555–557.

Grusby et al., "Casein expression in cytotoxic T lymphocytes", Proc. Natl. Acad. USA vol. 87, Sep. 1990, pp. 6897–6901.

Ebert et al., "Transgenic Production of a Variant of Human Tissue–Type Plasminogen Activator in Goat Milk: Generation of Transgenic Goats and Analysis of Expression", Bio/Technology vol. 9, No. 9, Sep. 1991, pp. 835–838.

Denman et al., "Transgenic Expression of a Variant of Human Tissue–Type Plasminogen Activator in Goat Milk: Purification and Characterization of the Recombinant Enzyme", Bio/Technology vol. 9, No. 9, Sep. 1991, pp. 839–843.

*Primary Examiner*—Deborah Crouch
*Assistant Examiner*—Deborah J. R. Clark
*Attorney, Agent, or Firm*—Frederick W. Pepper

[57] ABSTRACT

This invention relates to a process for producing a transgenic animal wherein gene expression regulatory region for a gene from chromosomal DNA is introduced in the animal to enable the expression of the desired exogenous gene in the animal. More specifically, this invention relates to a process in the field of transgenic animal technology wherein expression of a desired substance in a mammal is enabled by producing a recombinant expression vector capable of amplifying in a host cell such as *E. coli* by using a DNA fragment including a part of the structural gene coding for mC26 protein and sequences in the upstream and downstream of the mC26 gene that regulate the expression of the mC26 gene; and introducing the gene expression regulatory region for the mC26 gene in the animal by using the thus produced expression vector to produce a model animal for the gene expression regulatory experiment, and to thereby enable the expression of the desired substance in the mammary gland or other tissue of the animal.

5 Claims, 8 Drawing Sheets

| | | | | | | |
|---|---|---|---|---|---|---|
| GAATTCCCCA | AGGGACAGCT | TTAAATAAGA | AAACAACTCA | TTCAACAAAT | GCAAGCTAGA | 60 |
| ATATCCAGCA | AGAATTAAAT | TCTGTACTAA | ATACATTGAG | ATGCAGGGAT | AAACTAATAA | 120 |
| TGGTTCCAGT | ACTGAAAACT | GATCAACAAA | ACCAGTAAGA | TGCAAATCAT | ATAATTACTG | 180 |
| TAAAACTGGA | TATGTGTTAG | ACAATAAAGG | CTATAAGGCT | AGGGCCCAAA | TAAGTCTGTT | 240 |
| TGTCATTCTA | TTCCCCCAAA | GCTTGCAGAT | GGCTAGTACT | CAATAAATAG | TAGTAGGCCA | 300 |
| TGGTAGTGAA | CAAAGGTGGA | TACCACCAAT | AAGACACTGT | GGGGTCAGAT | GACTCACCAA | 360 |
| GGGAGACAAG | ATGATGAGGG | AAGTGGTTCA | AAATCAGCAG | AAAAGTCTAA | TAGAGAGCAG | 420 |
| GATGTAGAAA | CACCTCAGAC | AGATAGACAG | GAGAGCCTTC | TTGACAGAGC | AATAGCATGA | 480 |
| ACCTAGCATT | CCAGGGAAGA | AGGACCATCT | TGCAGAAGTC | AGGGATAAAG | TAGAAACGGT | 540 |
| AGAGGGCCAA | GATGTCTGAA | CTTTATCACT | AGAGGCTTTC | ACACAAAGAA | GTGACATGAC | 600 |
| CTCCAGGAGA | TCTCTCCAGT | ATTAACATGG | AAGGTAGACT | ATCATGTATG | ACAGAAGAGA | 660 |
| AGAAACTACT | ACCATAGCCT | AGTCTGGTGA | TGATGTATTT | TAAACGTACT | AGGGAATATG | 720 |
| TCTGTGGAAA | CCTCCCCACC | ATGGGCTTCC | TGTGAATGTC | TTCACCTGTC | CCCTCCTGTT | 780 |
| TGTAACTTCC | ATAGGCCATG | GAAGGATCAA | TGCTGGTGAG | AAGAAATCAG | ACAGGAAGGG | 840 |
| AGGTGAGAGG | CAACCCAAAA | CAAACTTCCT | TTACTACCTC | ATCTTGCCTA | AGGAGATCCC | 900 |
| AGATGTAGCA | AGAGGAAGAC | AAGACAAGGC | CTTGGAGCTT | CCTCTCAAGA | GAAGGAAGAC | 960 |
| TCACACTGGT | TGGCACAGCC | CAAGCTCTCC | TTGCTCTGAA | GGCTGGACTT | TATCCTGTGT | 1020 |
| CCAGCAAGCA | TGCACCTAAG | AGATATCTTG | GGATGCAGCA | GACCTTTCTT | GTCTGGAGAT | 1080 |
| GATCCAGAGG | GAGGTTTCAT | AGACATCATC | AAAACCTCTG | ATGAAGAAAG | AAACTAGTTC | 1140 |
| AATTCCTAAG | CCAGAATGAG | ACATTAATCC | TAGGTTTACC | CCCCATCTCC | TTTCCAGAGG | 1200 |
| CTTCCTCAGA | CATCCTACTG | CTCTATTTAA | AGTCACTAGA | TTCTGGAGGC | AGAATTAGAG | 1260 |
| TGGTCTACTT | TAAATAAACT | TTTTCTAAAC | TTACATACAT | ACATACATAT | ACATATATAC | 1320 |
| CAAGCCAAGG | CTATTTGATA | GACCATGTCT | CAAAAAAAAA | GAAAAATACA | GATATATAAT | 1380 |
| AGATTAGCTA | TATGAGAGAG | AGAGAGAGAG | AGAGAGAGAG | AGAGAGAGAG | AGAGAGAGGA | 1440 |
| <u>AGAAGAAGAA</u> | <u>GAAGAAGAAG</u> | <u>AAGAAGAAGA</u> | <u>AGAAGAAGAA</u> | <u>GAAGAAGAAG</u> | <u>AAGAAGAAGA</u> | 1500 |
| <u>AGAAGAAGAA</u> | <u>GAAGAAGAAG</u> | AAAAGGGAAA | TTAATTGGAA | AAAGAAAAGG | AACTCTCAGG | 1560 |
| ATGGAAAGGG | ACCAGAGAAG | GTAATATGGT | GTGCCATAAT | GAAGCCCTTT | ATTTTCCATA | 1620 |
| GTAAATCTGC | ACTAATGAAG | GAAGACATGC | ATACAAATAT | GTGCTTGGTA | GAAGCCACCT | 1680 |
| CATGACTTAA | ATATGAGTTT | CTTGATTAAT | AAATAACTTC | CCAAATATTA | TTAATCCTAT | 1740 |
| ATGAGCAAAC | CTAGCAGATG | GAATTGAACC | TGAACCTGCC | TCACTCCTCC | ATTCCTGAAC | 1800 |
| TGATGTGGAG | GATTATCTGC | ACCCTGGAGG | ACCATCTGGT | CTTTCCTTGA | TTCAGTCATA | 1860 |
| TAAGCAATAT | TTTCTGGACC | CAAGTATGAG | CCAGCTGCTA | GAGAGGTACT | GGAAAACCCA | 1920 |
| AGAAAGCAA | GAATAATCCC | AGCATCACAG | AAGTTTCACT | CTTCTGAAGG | AAACAGATAA | 1980 |
| TAATTAAATA | ATCAGATGGG | AAACTGTAAA | AATAATACCA | GTAATGGGTA | ACATTAAGGA | 2040 |
| TGGGAGTCTA | CTCAGGAAGT | TATCCCAAAG | GTACAAAGAG | ATGGCACCTG | GGCTGGCAC | 2100 |
| ACCATGGCAG | TAGCTAGGCC | AAAGGGAAGG | CTGGGGGCCT | TACTTTCTTG | CCAACTCATT | 2160 |
| TCCCAGAAAC | ACCAATTCCC | AAAACCCAAT | GTAGTCTGAA | TAGGAATTGG | AGGGGAAGCC | 2220 |
| TGGCTTGCTT | CCTGGTCTAA | TCTCCAACTA | TTGTCCAGCA | TCCTTACCCC | AAAATAAATA | 2280 |
| AAGCCCCAGC | AAGACTGCTA | CTCC | | | | |

*FIG. 4*

FIRST EXON                AGCATT CTACTCTGCT TCCCAGGGAA AGCTGACCTT 2340
GTTCCAGTGC CACCATGAAA TTCTTCACTG TCCTGCTATT TGTCAGTCTT GCTGCCACCT 2400
CTCTTGCTCT CCTGCCTG

FIRST INTRON     GT AAGTGCACCT TTCTTTCTGC TCTCCTTAGT CTCCTACAGG 2460
CCATGGGCTG TCAGGTAAGC AAAATTGCCA CCCTTGTGGA AAGATGATAA GACATGGAAT 2520
GAAAAAGCCA CAGCTGGATG TGGGCATGAA GACATATAGC TCATGAGTCC AGAAACCCAG 2580
AAAACCAAGG CTGGGTTCAG AGGCTAGACT GAACCCATAA CAGGGCAGAC TATCAGTCAA 2640
CAGAGATTCT GTTAGATCCT ATCACCAGAG GCTTGATCAG CACAACCCAA GTAAAATCAC 2700
TGCTTTAGAC ATCCTTAGCT CCCTTGGTAC AATGAGAGCA AGATGCACAC ACCACATCAA 2760
GTGCTATCCA TAGCACTCAC TCTGTACCAT ATAGTTCCAG GAACTTAGAA TACACTAACA 2820
GCTTACATAA AGATCTGTCA TCATTGAAAT TTCATTAGAG AAAGAAGAAA AAATAAACAT 2880
ACTAAAAATA TTATATAGTA TTTTAGAAAT GCTAAGGGAA GTGTAGAGAA GAGAAACATA 2940
AGGGACTAGC TAGGCATGGT GGTGCACACC TGCATTTCCA ACACTCAGGA AGCAGAAGCA 3000
GAACTACTAA GCAAAACCCT ATCTAAAGCA AACAAACCAC AAAGAGTAAG GGAGGTTGAG 3060
GAAGCTGCAA TGAGGTAACT ACAAATGACC AGTTCACATG TTACTTGTCT TGAGATCTCT 3120
GGAGATTTTA TCTTCTCTCC TCAG

SECOND EXON         GGTCCA AAGATGAACT TCAAATGAAG ACTCAGCCCA 3180
CAGATGCC

SECOND INTRON
      AG TAAGTCTCAT GAGAGCATCT CTTAATTGTT GGTAGCAAAA GACTAGAGAG 3240
TAAATGATGT TAGGAGAAAG TGAACAAACA GTTCCTCATG CTGTTGGCCT TAATTCTGCC 3300
TGCTGCACTG ATGGGCCATA AATCTGGGGG GTAGGAACAT TTTGTATAGC ACTTATGCTA 3360
TATAGTCATT GGAAATTGGA ATGGGGACAG CATTTCATAC CCAAGAGCTG ACAGGTAATA 3420
TTTCAGCTCA CCCAAAGACA AGTGGGAGCA GGGGGGGAGG GGTCTCTTCA GTTATAGGCA 3480
CTGTACTACA CAGCCCAAAA AAAAAAAAAA ACTTAAGCAT TGATGGGCTC AGATTTGAAG 3540
ATGCATTGTA AAGATTGTTT AATCATGAGC TATTTTCCCA AATTAACCTG GGAAAACTCT 3600
GAGAAGCTAA AAGAGAAAAA CACTTGGTGT TCAGAAGGAA GAACCAAGGT TAAGAAGCTT 3660
CTCATGTAAG TCAAGCAAAG GGTGAGGTGT TTACAAATGT CTCTTAATCA AGAAGGTGGG 3720
TTTTCCTGGG GTTGAAGTAG CAGAAATTCT TAATCGTATC ATTAGAAATC TAATTCATGC 3780
CTTTGAGGAG CTCAGGAAGA TAAATGCTAG CATAGAACCC CAATGCTACT GTAGATCAGT 3840
TAGGCAATTA CTCAACACTA ATGCACCATG TGAAGAGACA CTTTTTCTCC CAGATTTCTC 3900
TGCCCCTCAC TCCCTACATG TCCTTAG                                       2220

THIRD EXON             TTC CAGCTGCCCA GTCCACTCCC ACCAGCTACA 3960
CCAGTGAGGA GAGTACTTCC AGTAAGGACC TTTCCAAGGA GCCTTCCATC TTCAGAGAAG 4020
AGCTGATTTC CAAAGATAAT GTGGTGATAG AATCTACCAA GCCAGAGAAT CAAGAGGCCC 4080
AGGATGGGCT CAGGAGCGGG TCATCTCAGC TGGAAGAGAC CACAAGACCC ACCACCTCAG 4140
CTG

THIRD INTRON
    GTATGAG CCAGGGAAGA AGGAAGATGT CTTGGGAGGT GGTAAGCAGA GGAAGACAGG 4200
GCAGACAGTA GCTTGTATAA ATAGGAGGCT CTACAAAGGA AAAAGAAGTC CTAGAAGGAC 4260
AAATTTTAAG TGTAAACCAA CTGCCAGCAC TGCAGGAAGC TGTTGGGATG GGAGGATGGA 4320
GGTGTGAATG GGAACCCACT GTAACTGGAC ATTTCTATCT TCAAATTACA G

FOURTH EXON                                       CAACCACCT 4380
CAGAGGAAAA TCTGACCAAG TCAAGCCAGA CAGTGGAGGA AGAACTGGGT AAAATAATTG 4440
AAGGATTTGT AACTGGTGCA GAAGACATAA TCTCTGGTGC CAGTCGTATC ACGAAGTCAT 4500
GAAGACAAAA ACACCTAACC ACTAAGTCCC ATGCTAGGTG GTGCCTTCAT CAGCCACATT 4560
CTGCTCATCT GACCACCACC TCTCAGTCTG CCCTTTGATG TCTTACATTA AAGTATTGCA 4620
ACCT

*FIG. 5*

```
            AAACCC  GGCTCTCTGC  TGGCTTTGTC  AGACCGGGGA  AAGTAAAGGT  TAGGGTTAGG  4680
        TTGGATTTCT  CTTTAGCTAC  TCTATCCTTT  TAGAATAGAA  TAAACCAAAC  CTCTCACACA  4740
        CACAACCCTC  AGTTTACAAG  CCCAGTCAAG  TCTCCCCATC  CAAAACAACC  TCTGCAAAAA  4800
        CTTGATCCTT  GTCATCCATC  TGTTCCTCCA  ATATAGACAA  CCTCCTTTCC  TACTCACCAT  4860
        AGCCTACCTG  CTCCCACACA  CCAGCCCATT  ATAGTTGCTC  TCCCAAAGGC  CACATACAGC  4920
        AACAGCCCTC  ATGGCCTTCT  TAGTTCTGGC  TTTTCTACTC  TAGCTCTGAA  AGACTGGAAG  4980
        CAACTATTTC  CTCTAGAATC  TTCTCCTCAC  TAATTTTCTT  TGCCACTTTT  GATTATTCAA  5040
        TCTCCCTGCT  CCTTTTCTGA  ACTGTTTGGT  ATCTAATCCT  AGATCCCATC  CTGTACTCTC  5100
        TTGCCTTCAT  CTCTCTTCAG  GATTCCCATA  GCCTCATCTG  TCAGGACTTC  TTATTAACCC  5160
        ACACAGCTAA  CATCCACCAA  GTGCCCATCA  GACCTGCCTA  CCTAATTTGC  TCTGACTTTC  5220
        CTGCAACCCT  AAGCAGTTTT  CACTATGAAT  GCATACAAAA  CATGGAGAAA  TGAAAACACA  5280
        GGAAAAGAAG  ACTGCCTATG  CAAGAGTAGG  GATGAGAGGC  ATCACTGCTC  TCCAGCATCC  5340
        TACCCCCAGC  TTACATGAAA  GGAAGCTCAA  GAGATTAACA  GAGCAACTAA  GCTT        5394
```

FIG. 6

* Enzymes that did NOT cut a fragment (>500bp) out of the insert mC26 DNA. Restriction sites shown in italics are presumed from the DNA sequence data.

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 5394 base pairs
      (B) TYPE: nucleic acid
      (C) STRANDEDNESS: double
      (D) TOPOLOGY: linear (ii) MOLECULE TYPE: DNA (genomic)

(ix) FEATURE:

(A) NAME/KEY: CAAT_signal
        (B) LOCATION: 2234..2243

(ix) FEATURE:
        (A) NAME/KEY: TATA_signal
        (B) LOCATION: 2275..2281

(ix) FEATURE:
        (A) NAME/KEY: polyA_signal
        (B) LOCATION: 4607..4612

(xi) SEQUENCE DESCRIPTION: SEQ ID NO:1:

```
GAATTCCCCA AGGGACAGCT TTAAATAAGA AAACAACTCA TTCAACAAAT GCAAGCTAGA       60

ATATCCAGCA AGAATTAAAT TCTGTACTAA ATACATTGAG ATGCAGGGAT AAACTAATAA      120

TGGTTCCAGT ACTGAAAACT GATCAACAAA ACCAGTAAGA TGCAAATCAT ATAATTACTG      180

TAAAACTGGA TATGTGTTAG ACAATAAAGG CTATAAGGCT AGGGCCCAAA TAAGTCTGTT      240

TGTCATTCTA TTCCCCCAAA GCTTGCAGAT GGCTAGTACT CAATAAATAG TAGTAGGCCA      300

TGGTAGTGAA CAAAGGTGGA TACCACCAAT AAGACACTGT GGGGTCAGAT GACTCACCAA      360

GGGAGACAAG ATGATGAGGG AAGTGGTTCA AAATCAGCAG AAAAGTCTAA TAGAGAGCAG      420

GATGTAGAAA CACCTCAGAC AGATAGACAG GAGAGCCTTC TTGACAGAGC AATAGCATGA      480

ACCTAGCATT CCAGGGAAGA AGGACCATCT TGCAGAAGTC AGGGATAAAG TAGAAACGGT      540

AGAGGGCCAA GATGTCTGAA CTTTATCACT AGAGGCTTTC ACACAAAGAA GTGACATGAC      600

CTCCAGGAGA TCTCTCCAGT ATTAACATGG AAGGTAGACT ATCATGTATG ACAGAAGAGA      660

AGAAACTACT ACCATAGCCT AGTCTGGTGA TGATGTATTT TAAACGTACT AGGGAATATG      720

TCTGTGGAAA CCTCCCCACC ATGGGCTTCC TGTGAATGTC TTCACCTGTC CCCTCCTGTT      780

TGTAACTTCC ATAGGCCATG GAAGGATCAA TGCTGGTGAG AAGAAATCAG ACAGGAAGGG      840

AGGTGAGAGG CAACCCAAAA CAAACTTCCT TTACTACCTC ATCTTGCCTA AGGAGATCCC      900

AGATGTAGCA AGAGGAAGAC AAGACAAGGC CTTGGAGCTT CCTCTCAAGA GAAGGAAGAC      960

TCACACTGGT TGGCACAGCC CAAGCTCTCC TTGCTCTGAA GGCTGGACTT TATCCTGTGT     1020

CCAGCAAGCA TGCACCTAAG AGATATCTTG GGATGCAGCA GACCTTTCTT GTCTGGAGAT     1080

GATCCAGAGG GAGGTTTCAT AGACATCATC AAAACCTCTG ATGAAGAAAG AAACTAGTTC     1140

AATTCCTAAG CCAGAATGAG ACATTAATCC TAGGTTTACC CCCCATCTCC TTTCAGAGG      1200

CTTCCTCAGA CATCCTACTG CTCTATTTAA AGTCACTAGA TTCTGGAGGC AGAATTAGAG     1260

TGGTCTACTT TAAATAAACT TTTTCTAAAC TTACATACAT ACATACATAT ACATATATAC     1320

CAAGCCAAGG CTATTTGATA GACCATGTCT CAAAAAAAAA GAAAAATACA GATATATAAT     1380

AGATTAGCTA TATGAGAGAG AGAGAGAGAG AGAGAGAGAG AGAGAGAGAG AGAGAGAGGA     1440

AGAAGAAGAA GAAGAAGAAG AAGAAGAAGA AGAAGAAGAA GAAGAAGAAG AAGAAGAAGA     1500

AGAAGAAGAA GAAGAAGAAG AAAAGGGAAA TTAATTGGAA AAAGAAAAGG AACTCTCAGG     1560

ATGGAAAGGG ACCAGAGAAG GTAATATGGT GTGCCATAAT GAAGCCCTTT ATTTTCCATA     1620

GTAAATCTGC ACTAATGAAG GAAGACATGC ATACAAATAT GTGCTTGGTA GAAGCCACCT     1680

CATGACTTAA ATATGAGTTT CTTGATTAAT AAATAACTTC CCAAATATTA TTAATCCTAT     1740

ATGAGCAAAC CTAGCAGATG GAATTGAACC TGAACCTGCC TCACTCCTCC ATTCCTGAAC     1800

TGATGTGGAG GATTATCTGC ACCCTGGAGG ACCATCTGGT CTTTCCTTGA TTCAGTCATA     1860

TAAGCAATAT TTTCTGGACC CAAGTATGAG CCAGCTGCTA GAGAGGTACT GGAAAACCCA     1920

AGAAAAGCAA GAATAATCCC AGCATCACAG AAGTTTCACT CTTCTGAAGG AAACAGATAA     1980

TAATTAAATA ATCAGATGGG AAACTGTAAA AATAATACCA GTAATGGGTA ACATTAAGGA     2040
```

```
TGGGAGTCTA CTCAGGAAGT TATCCCAAAG GTACAAAGAG ATGGCACCTG GGGCTGGCAC    2100

ACCATGGCAG TAGCTAGGCC AAAGGGAAGG CTGGGGGCCT TACTTTCTTG CCAACTCATT    2160

TCCCAGAAAC ACCAATTCCC AAAACCCAAT GTAGTCTGAA TAGGAATTGG AGGGGAAGCC    2220

TGGCTTGCTT CCTGGTCTAA TCTCCAACTA TTGTCCAGCA TCCTTACCCC AAAATAAATA    2280

AAGCCCCAGC AAGACTGCTA CTCCAGCATT CTACTCTGCT TCCCAGGGAA AGCTGACCTT    2340

GTTCCAGTGC CACCATGAAA TTCTTCACTG TCCTGCTATT TGTCAGTCTT GCTGCCACCT    2400

CTCTTGCTCT CCTGCCTGGT AAGTGCACCT TTCTTTCTGC TCTCCTTAGT CTCCTACAGG    2460

CCATGGGCTG TCAGGTAAGC AAAATTGCCA CCCTTGTGGA AGATGATAA GACATGGAAT     2520

GAAAAGCCA CAGCTGGATG TGGGCATGAA GACATATAGC TCATGAGTCC AGAAACCCAG     2580

AAAACCAAGG CTGGGTTCAG AGGCTAGACT GAACCCATAA CAGGGCAGAC TATCAGTCAA    2640

CAGAGATTCT GTTAGATCCT ATCACCGAGA GCTTGATCAG CACAACCCAA GTAAAATCAC    2700

TGCTTTAGAC ATCCTTAGCT CCCTTGGTAC AATGAGAGCA AGATGCACAC ACCACATCAA    2760

GTGCTATCCA TAGCACTCAC TCTGTACCAT ATAGTTCCAG GAACTTAGAA TACACTAACA    2820

GCTTACATAA AGATCTGTCA TCATTGAAAT TTCATTAGAG AAAGAAGAAA AATAAACAT     2880

ACTAAAAATA TTATATAGTA TTTTAGAAAT GCTAAGGGAA GTGTAGAGAA GAGAAACATA    2940

AGGGACTAGC TAGGCATGGT GGTGCACACC TGCATTTCCA ACACTCAGGA AGCAGAAGCA    3000

GAACTACTAA GCAAAACCCT ATCTAAAGCA AACAAACCAC AAAGAGTAAG GGAGGTTGAG    3060

GAAGCTGCAA TGAGGTAACT ACAAATGACC AGTTCACATG TTACTTGTCT TGAGATCTCT    3120

GGAGATTTTA TCTTCTCTCC TCAGGGTCCA AGATGAACT TCAAATGAAG ACTCAGCCCA     3180

CAGATGCCAG TAAGTCTCAT GAGAGCATCT CTTAATTGTT GGTAGCAAAA GACTAGAGAG    3240

TAAATGATGT TAGGAGAAAG TGAACAAACA GTTCCTCATG CTGTTGGCCT TAATTCTGCC    3300

TGCTGCACTG ATGGGCCATA AATCTGGGGG GTAGGAACAT TTTGTATAGC ACTTATGCTA    3360

TATAGTCATT GGAAATTGGA ATGGGACAG CATTTCATAC CCAAGAGCTG ACAGGTAATA     3420

TTTCAGCTCA CCCAAAGACA AGTGGGAGCA GGGGGGGAGG GGTCTCTTCA GTTATAGGCA    3480

CTGTACTACA CAGCCCAAAA AAAAAAAAAA ACTTAAGCAT TGATGGGCTC AGATTTGAAG    3540

ATGCATTGTA AAGATTGTTT AATCATGAGC TATTTTCCCA AATTAACCTG GGAAAACTCT    3600

GAGAAGCTAA AAGAGAAAAA CACTTGGTGT TCAGAAGGAA GAACCAAGGT TAAGAAGCTT    3660

CTCATGTAAG TCAAGCAAAG GGTGAGGTGT TTACAAATGT CTCTTAATCA AGAAGGTGGG    3720

TTTTCCTGGG GTTGAAGTAG CAGAAATTCT TAATCGTATC ATTAGAAATC TAATTCATGC    3780

CTTTGAGGAG CTCAGGAAGA TAAATGCTAG CATAGAACCC CAATGCTACT GTAGATCAGT    3840

TAGGCAATTA CTCAACACTA ATGCACCATG TGAAGAGACA CTTTTTCTCC CAGATTTCTC    3900

TGCCCCTCAC TCCCTACATG TCCTTAGTTC CAGCTGCCCA GTCCACTCCC ACCAGCTACA    3960

CCAGTGAGGA GAGTACTTCC AGTAAGGACC TTTCCAAGGA GCCTTCCATC TTCAGAGAAG    4020

AGCTGATTTC CAAAGATAAT GTGGTGATAG AATCTACCAA GCCAGAGAAT CAAGAGGCCC    4080

AGGATGGGCT CAGGAGCGGG TCATCTCAGC TGGAAGAGAC CACAAGACCC ACCACCTCAG    4140

CTGGTATGAG CCAGGGAAGA AGGAAGATGT CTTGGGAGGT GGTAAGCAGA GGAAGACAGG    4200

GCAGACAGTA GCTTGTATAA ATAGGAGGCT CTACAAAGGA AAAAGAAGTC CTAGAAGGAC    4260

AAATTTTAAG TGTAAACCAA CTGCCAGCAC TGCAGGAAGC TGTTGGGATG GGAGGATGGA    4320

GGTGTGAATG GGAACCCACT GTAACTGGAC ATTTCTATCT TCAAATTACA GCAACCACCT    4380

CAGAGGAAAA TCTGACCAAG TCAAGCCAGA CAGTGGAGGA AGAACTGGGT AAAATAATTG    4440
```

```
AAGGATTTGT AACTGGTGCA GAAGACATAA TCTCTGGTGC CAGTCGTATC ACGAAGTCAT    4500

GAAGACAAAA ACACCTAACC ACTAAGTCCC ATGCTAGGTG GTGCCTTCAT CAGCCACATT    4560

CTGCTCATCT GACCACCACC TCTCAGTCTG CCCTTTGATG TCTTACATTA AAGTATTGCA    4620

ACCTAAACCC GGCTCTCTGC TGGCTTTGTC AGACCGGGGA AAGTAAAGGT TAGGGTTAGG    4680

TTGGATTTCT CTTTAGCTAC TCTATCCTTT TAGAATAGAA TAAACCAAAC CTCTCACACA    4740

CACAACCCTC AGTTTACAAG CCCAGTCAAG TCTCCCCATC CAAAACAACC TCTGCAAAAA    4800

CTTGATCCTT GTCATCCATC TGTTCCTCCA ATATAGACAA CCTCCTTTCC TACTCACCAT    4860

AGCCTACCTG CTCCCACACA CCAGCCCATT ATAGTTGCTC TCCCAAAGGC CACATACAGC    4920

AACAGCCCTC ATGGCCTTCT TAGTTCTGGC TTTTCTACTC TAGCTCTGAA AGACTGGAAG    4980

CAACTATTTC CTCTAGAATC TTCTCCTCAC TAATTTTCTT TGCCACTTTT GATTATTCAA    5040

TCTCCCTGCT CCTTTTCTGA ACTGTTTGGT ATCTAATCCT AGATCCCATC CTGTACTCTC    5100

TTGCCTTCAT CTCTCTTCAG GATTCCCATA GCCTCATCTG TCAGGACTTC TTATTAACCC    5160

ACACAGCTAA CATCCACCAA GTGCCCATCA GACCTGCCTA CCTAATTTGC TCTGACTTTC    5220

CTGCAACCCT AAGCAGTTTT CACTATGAAT GCATACAAAA CATGGAGAAA TGAAAACACA    5280

GGAAAAGAAG ACTGCCTATG CAAGAGTAGG GATGAGAGGC ATCACTGCTC TCCAGCATCC    5340

TACCCCAGC TTACATGAAA GGAAGCTCAA GAGATTAACA GAGCAACTAA GCTT          5394

(2) INFORMATION FOR SEQ ID NO:2:

(i) SEQUENCE CHARACTERISTICS:
        (A) LENGTH: 357 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:2:

GACGAGAAGA CGATGCAGAA AGCCAGGCGG AGGCAGTGGG ATGAGCCACG GGTCTGCTCC     60

AGGCGGTACC TGAAAGTGGA CTTTGCGGAC ATCGGGTGGA ATGAATGGAT CATCTCCCCG    120

AAATCCTTCG ATGCCTACTA CTGCGCGGGG GCCTGCGAGT TCCCCATGCC CAAGATTGTC    180

CGCCCATCCA ATCATGCCAC CATCCAGGGC ATCGTCAGAG CGGTGGGCAT CGTCCCTGGC    240

ATCCCGGAGC CCTGTTGTGT TCCAGACAAG ATGAACTCCC TTGGAGTCCT TTTCCTGGAT    300

GAGAACCGGA ACGCGGTTCT GAAGGTGTAC CCCAACATGT CCGTGGACAC CTGTGCA       357

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:3:

GTGCCACCAT GAAATTCTTC                                                 20

(2) INFORMATION FOR SEQ ID NO:4:

(i) SEQUENCE CHARACTERISTICS:
        (A) LENGTH: 20 base pairs
        (B) TYPE: nucleic acid
```

-continued

```
            (C) STRANDEDNESS: single
            (D) TOPOLOGY: linear (ii) MOLECULE TYPE: other nucleic acid
            (A) DESCRIPTION: /desc = "Synthetic DNA"

(xi) SEQUENCE DESCRIPTION: SEQ ID NO:4:

TGGCTTGCTT CCTGGTCTAA                                                    20

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA"

(xi) SEQUENCE DESCRIPTION: SEQ ID NO:5:

TTGCTTCCTG GTCTAATCTC                                                    20

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA"

(xi) SEQUENCE DESCRIPTION: SEQ ID NO:6:

CTCTGCTTCC CAGGGAAAGC                                                    20

(2) INFORMATION FOR SEQ ID NO:7:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA"

(xi) SEQUENCE DESCRIPTION: SEQ ID NO:7:

GACGAGAAGA CGATGCAGA                                                     19

(2) INFORMATION FOR SEQ ID NO:8:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA"

(xi) SEQUENCE DESCRIPTION: SEQ ID NO:8:

GCACAGGTGT CCACGGACA                                                     19
```

MC26 GENE EXPRESSION-REGULATORY REGION

BACKGROUND OF THE INVENTION

This invention relates to a process for producing a transgenic animal wherein gene expression regulatory region for a gene from chromosomal DNA is introduced in the animal to enable the expression of the desired exogenous gene in the animal. More specifically, this invention relates to a process in the field of transgenic animal technology wherein expression of a desired substance in a mammal is enabled by producing a recombinant expression vector capable of amplifying in a host cell such as E. coli by using a DNA fragment including a part of the structural gene coding for mC26 protein and sequences in the upstream and downstream of the mC26 gene that regulate the expression of the mC26 gene; and introducing the gene expression regulatory region for the mC26 gene in the animal by using the thus produced expression vector to produce a model animal for the gene expression regulatory experiment, and to thereby enable the expression of the desired substance in the mammary gland or other tissue of the animal.

In the production of a substance involving use of a genetically manipulated recombinant gene, cultures of microorganisms such as Eschrichia coli, Bacillus subtilis and yeast and various other cells of animal and vegetable origins are used for the host system. The thus produced gene may be introduced in the animal to produce a transgenic animal, and the recombinant gene may be expressed in the transgenic animal to thereby produce the recombinant protein (Palmiter et al., Cell, 29, 701–710, 1982).

In a typical process, a solution containing the recombinant DNA is introduced in the embryo (oosperm) to produce a transgenic animal where the gene introduced is expressed for protein synthesis (DiTullio et al., Bio/Technology, 10, 74–77, 1992). Another process that has been developed involves use of a retrovirus as an intermediate vector (Jaenisch et al., Cell, 24, 519, 1981). This process, however, is associated with a fair risk of oncogene activation and undesirable transcription. Also developed is a process in which the recombinant DNA is directly injected into the animal for the gene expression. This process, when carried out in an industrial scale, is not fully reliable due to insufficiency in gene expression efficiency and stability of the introduced gene.

The recombinant gene introduced in the production of a transgenic animal may be a genomic DNA or a cDNA complimentary to mRNA, and the recombinant DNA sequence introduced may optionally include desired gene expression regulatory regions such as promoter, enhancer, and transcription termination signal regions in the upstream or downstream of the structural gene.

Promoters and enhancer are each provided with different properties, and some lead to expression in a particular organ or tissue (tissue-specific expression) while others lead to expression at a particular timing of the growth (timing-specific expression) or expression in response to the stimulation by environment inside or outside the cell (stimulation-responsive expression). Expression at a desired timing at a desired site in the transgenic animal may be enabled by incorporating gene expression regulatory sequences for the structural gene which are different from the native promoter and the native enhancer upon the preparation of the recombinant sequence to be introduced in the animal (Japanese Patent Application Laid-Open No. 3(1991)-210187).

Various hormone-responsive elements, namely, regions in the gene that respectively respond to stimulus of a hormone such as prolactin, insulin, glucocorticoid, progesterone, estrogen, or the like are associated with alpha casein gene, which is a typical natural milk protein gene. As a consequence, alpha-casein gene is regulated to express in a timing- and tissue-specific manner, namely, to express in the mammary gland during its lactation stage. A recombinant sequence including the gene expression regulatory regions in addition to the milk protein gene undergoes a transcription and a translation as in the case of the natural milk protein gene, and as a consequence, the recombinant sequence is capable of secreting the protein coded by the recombinant gene (Japanese Patent Application Laid-Open No. 63(1988)-291). Secretion into milk of an exogenous gene product by utilizing an expression vector including a gene coding a whey protein (WAP, beta-lactoglobulin) has also been disclosed (Japanese Patent Application Laid-Open No. 63(1988)-291; PCT Application (Japan) Laid-Open No. 64(1989)-500162).

mC26 gene has been identified by Satow et al. (J. Biochem. 99, 1639–1643, 1986) as a gene whose gene product is expressed in mammary gland in a large amount in a lactation-specific and tissue-specific manner. The gene product of mC26 is the product identified by Dowbenko et al. (J. Bio. Chem., 268, 4525–4529, 1993) as leukocyte CAM (cell adhesion molecule), and is referred to as GLYCAM-1. The locus of mC26 has been mapped in mouse, and the nucleotide sequence of the region of the structural gene and a part of the region in the vicinity of the structural gene are already determined (Dowbenko et al., supra.) To an L cell having glucocorticoid receptors derived from mouse fibroblast cell was introduced mC26 gene after its cloning in order to investigate transitional expression and expression in the transformant cell. It was then found that actions of hormones to the mC26 gene is different from those found in conventional cases, and that the transcription product of the mC26 gene is an abnormal RNA that is different from the known mRNA. Difference in the gene expression regulation mechanism of the mC26 gene from those of the known casein genes was thus revealed (Kawamura et al., J. Biochem. 101, 103–110, 1987).

SUMMARY OF THE INVENTION

In view of such situation, the inventors of the present invention have carried out an investigation to find out the mechanisms of mC26 expression system, in particular, transcription enhancer/promoter regions to thereby promote effective expression of the exogenous gene and establish a model animal for gene expression regulation experiment that has incorporated therein the mC26 gene expression regulatory region; and furthermore, to establish a technique in the field of transgenic animals that would enable production of a desired substance in the mammary gland of a mammal.

An object of the present invention is to provide a process in the field of transgenic animal technology wherein expression of a desired substance in the mammary gland of a mammal is enabled by producing a recombinant expression vector capable of amplifying in a host cell such as E. coli by using a genomic DNA fragment including the structural gene coding for mC26 protein and sequences in the vicinity of the mC26 gene that are involved in the expression of the mC26 gene; and introducing the gene expression regulatory region for the mC26 gene in the animal by using the thus produced expression vector to produce a model animal for the gene expression regulatory experiment, and to thereby enable the expression of the desired substance in the mammary gland or other tissue of the animal.

It has been determined the sequence of the genomic DNA in the region including the mC26 structural gene and the gene expression regulatory regions in the vicinity of the mC26 structural gene, in particular, the region of the enhancer/promoter located on the 5' upstream side of the structural gene, and prepared a recombinant expression vector including the DNA of the region. By using the thus prepared vector, it has also been confirmed that the gene expression regulatory region for the mC26 gene is regulated in the animal cell, and that the desired exogenous gene has been introduced in the mammary gland of the recipient animal actually expressing the exogenous gene product. The present invention has been completed on such findings.

BRIEF DESCRIPTION OF THE DRAWINGS

FIG. 4 sequences of SEQ ID No. 1 shows the 5' upstream expression regulatory region of mC26 gene. The underlined region is MobII repeats.

FIG. 5 sequences of SEQ ID No. 1 shows the structural gene region of mC26 gene. The nucleotide numbers are in common with FIG. 4 and SEQ ID No. 1.

FIG. 6 sequences of SEQ ID No. 1 shows the 3' downstream expression regulatory region of mC26 gene. The nucleotide numbers are in common with FIGS. 4 and 5, sequences of SEQ ID No. 1 and SEQ ID No. 1.

DETAILED DESCRIPTION OF THE INVENTION

Figure 1:
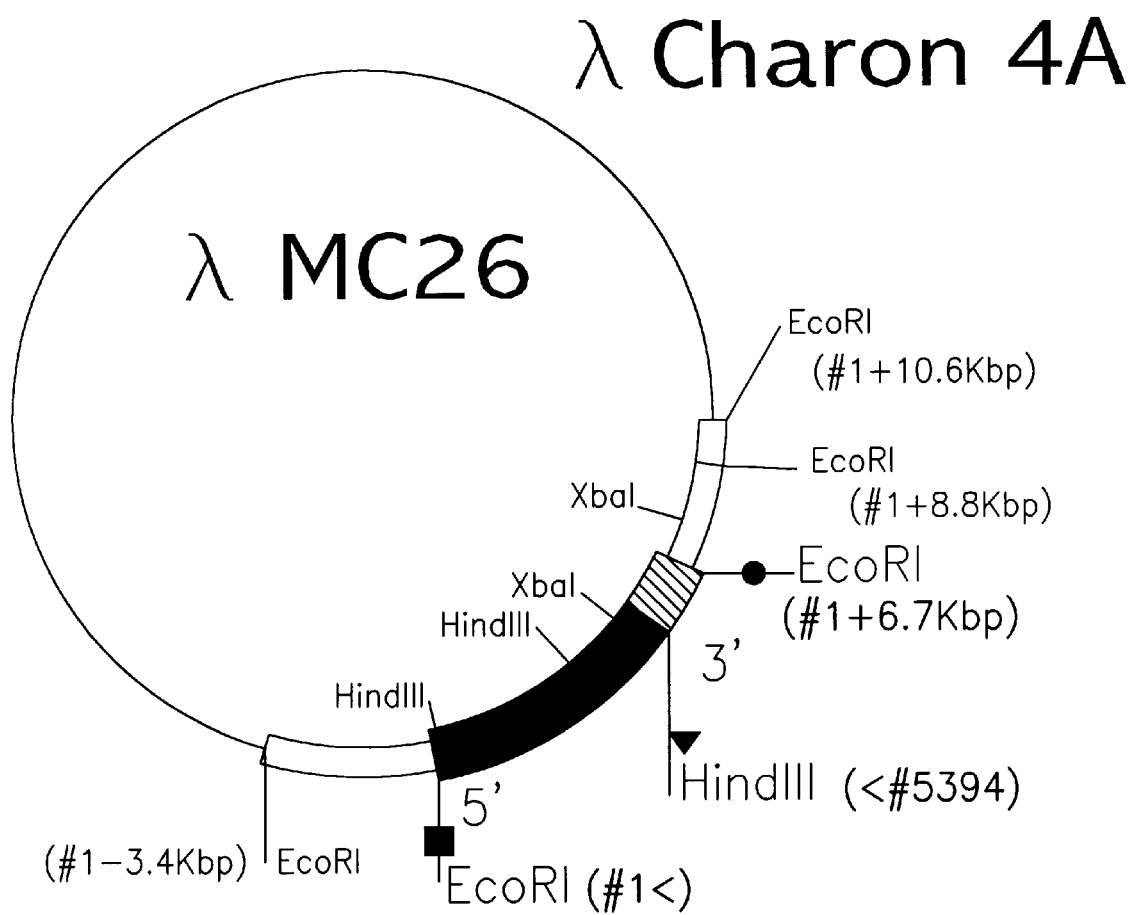
FIG. 1 is a restriction enzyme map of λmC26. The region shown by the solid line is derived from λcharon4A. The region other than the region shown by the solid line, namely, the region shown by the frame is the EcoRI fragment of about 12.7 kb from the EcoRI (#1–3.4 kbp) to the EcoRI (#1+10.6 kbp). #1 corresponds to nucleotide number 1 of the SEQ ID No. 1, and the indications of 5' and 3' are those for the mC26 structural gene.

According to the present invention, there is provided a DNA fragment, which may -serve an expression cassette, comprising
(i) expression regulatory region of 2304 bp shown in FIG. 4 sequences of SEQ ID No. 1 located in the 5' upstream side of the mC26 gene;

(ii) region of the mC26 structural gene of 2320 bp shown in FIG. 5; sequences of SEQ ID No. 1 and
(iii) expression regulatory region of 770 bp shown in FIG. 6 sequences of SEQ ID No. 1 located in the 3' downstream side of the mC26 gene arranged in the direction of transcription.

According to one aspect of the invention, there is provided an expression cassette wherein the region (ii) is fully or partly substituted with another exogenous gene, or alternatively, the region (ii) has another exogenous gene inserted in at lease one site therein. The exogenous gene inserted is not limited to any particular gene.

In the preparation of the expression cassette, it is desirable that (1) a signal sequence is included for the purpose of promoting extracellular secretion of the exogenous gene protein linked in the downstream by incorporation of first exon (2305th nucleotide to 2418th nucleotide in SEQ ID No. 1) in FIG. 5; and (2) second exon (3145th nucleotide to 3188th nucleotide in SEQ ID No. 1), third exon (3928th nucleotide to 4143rd nucleotide in SEQ ID No. 1), and fourth exon (4372nd nucleotide to 4624th nucleotide in SEQ ID No. 1) in FIG. 5 are cleaved/deleted, and all or some of first intron (2419th nucleotide to 3144th nucleotide in SEQ ID No. 1), second intron (3189th nucleotide to 3927th nucleotide in SEQ ID No. 1), and third intron (4144th nucleotide to 4371st nucleotide in SEQ ID No. 1) in FIG. 5 that are likely to be involved splicing are included in linked form to improve the expression efficiency. Such factor may be suitably selected in each case depending on the secretion efficiency of the exogenous gene product, type of the exogenous gene, linkage susceptibility of the recombinant DNA, and the like.

According to one aspect of the invention, there is provided a process for producing a transgenic animal comprising the steps of constructing an expression vector including the above-described expression cassette, and introducing the expression vector in the embryonic cell of a mammal. In such transgenic animal production process, a DNA fragment extending further to the 5' upstream side of the (i) and a DNA fragment extending further to the 3' downstream side of the (iii) may be used instead of the regions (i) and (iii), respectively. Exemplary fragments that can be used include the EcoRI fragment of about 12.7 kb in FIG. 1 and the EcoRI fragment of about 6.7 kb in FIG. 2.

Those skilled in the art will readily appreciate that a part or the entire length of the DNA fragment having the sequence of FIG. 4 or 6 sequences of SEQ ID No. 1 may be used as an expression regulatory region for expressing any one of the genes known in the art, and such use may constitute another aspect of the invention.

The term "vector" used herein is contemplated to designate the vector of either plasmid origin or bacteriophage origin. In the present invention, the preferred are the vectors of *E. coli* origin, and the most preferred is λ phage. The vector used is not limited to such species.

In the present invention, the term "EcoRI fragment" designates the DNA fragment whose opposite ends are recognizable with EcoRI, and the term "EcoRI-HindIII fragment" designates the DNA fragment whose opposite ends are respectively recognizable with EcoRI and HindIII. Other designations of fragments including the name of other restriction enzymes may be equivalently understood.

In the specification, the size of the DNA fragment shown to the first decimal place (for example, 0.1 kb) is an approximate size of the sequence determined by electrophoresis in contrast to the sequence whose length is clearly represented by an integer. Those skilled in the art will readily appreciate that there may be some difference between the nucleotide number (bp) indicated in the specification and the nucleotide number of actually existing DNA fragment.

It should be noted that the expression regulatory region shown in FIG. 4 sequences of SEQ ID No. 1 located in the 5' upstream side of the mC26 gene, and the expression regulatory region shown in FIG. 6 sequences of SEQ ID No. 1 located in the 3' downstream side of the mC26 gene have been partly published in Dowbenko et al., supra. It is, however, the present invention that has for the first time revealed the necessity of such regions including the portion whose sequence has never been found out for the expression of the exogenous gene in a substantial scale.

In the present invention, the recombinant DNA technique commonly used in the art has been carried out, unless otherwise noted, in accordance with:

Sambrook, Fristch, and Maniatis, "Molecular Cloning", Cold Spring Harbour Press, 1989; and Davis, Dibner and Batty, "Basic Methods in Molecular Biology", Elsevier, New York, 1986.

(1) Preparation of DNA fragment

The DNA fragments of the region of the mC26 structural gene (FIG. 5); sequences of SEQ ID No. 1 the expression regulatory region located in the 5' upstream side of the mC26 structural gene (FIG. 4); sequences of SEQ ID No. 1 and the expression regulatory region located in the 3' downstream side of the mC26 structural gene (FIG. 6) sequences of SEQ ID No. 1 used in the present invention may be simultaneously or separately obtained from a mouse genomic DNA library in accordance with a known method.

The non-limiting preferable processes that may be used in the present invention include the conventional process using an oligomer probe; and the two processes, namely, oligo(dT) primed reaction and random primed reaction using the cDNA probe prepared from a messenger RNA; and the messenger RNA primed process directly using the a mRNA for the probe. (i) Process using the oligomer DNA probe The probe used for the oligomer DNA probe process may preferably be the one with a length of about 20 nucleotides or longer which is free from the sequence found in chromosomal DNA at a high frequency.

Preferably, the probe used is at least one sequence in the first exon of mC26 gene selected from:

5' GTGCCACCATGAAATTCTTC 3' (SEQ ID NO. 3);

5' TGGCTTGCTTCCTGGTCTAA 3' (SEQ ID NO. 4);

5' TTGCTTCCTGGTCTAATCTC 3' (SEQ ID NO. 5); and

5' CTCTGCTTCCCAGGGAAAGC 3' (SEQ ID NO. 6).

The sequences used, however, are not limited to such sequences.

The labeling of the synthesized DNA may be carried out by a non-limiting method such as radiolabeling. The selection of the DNA of the mC26 gene from the mouse genomic DNA library by the use of the labeled probe may be carried out by a conventional method (See, Sambrook et al., Molecular Cloning, supra). Commercially available human and mouse genomic libraries may be used in such process.

When a gene corresponding to the mC26 in an animal of the species other than mouse is to be obtained, it is necessary to take the variation in the nucleotide sequences between the different animal species into consideration. It would be necessary to lower the selectability by changing the hybridization temperature or the formulation of the reaction solution. It is also desirable to take the degeneration of the codon into consideration. Such process may be carried out by a standard process in the art using commercially available reagents and commercially available equipment.

(ii) Messenger RNA primed process

The mRNA used for the messenger RNA primed process is isolated by a standard process. The animal used may preferably be human, goat, or mouse although the animal used is not limited to any particular species. The tissue used may preferably be mammary gland during its peak lactation although the tissue used is not limited to any particular type. The primers typically used in the preparation of the cDNA probe from the mRNA are oligo(dT) primer and random (hexamer) primer, both of which are commercially available, and these primers are labeled by a standard method. In addition to the cDNA probes prepared by using such primers, a cap-labeled probe which is a probe having a labeled cap structure region may be prepared for use in the screening. The labeling of such a probe may be carried out in accordance with the manufacturer's manual by using a commercially available radio labeled cap analogue or guanylyl transferase (for example, the product of Bethesda Research Inc.).

The screening with the above-described cDNA may be carried out by a standard process. In view of the fact that length of the exon is as short as several tens of bp in many genes, use of a long probe is not always necessary, and it is rather preferable to separately use a relatively long probe of about 500 bp and a relatively short probe of about 30 bp to compare the results.

The animal used for the construction of the genomic library may preferably be a mammal, and use of cow, goat, rabbit, rat or mouse is preferable. Commercially available genomic DNA library can be used when the animal used is human, mouse, or the like. The DNA is totally or partly digested with a restriction enzyme to cleave the DNA into the DNA fragments of 15 to 20 bp. Preferably, the non-limiting restriction enzyme used is EcoRI. The extraction of the chromosomal DNA, the cleavage with the restriction enzyme, and the ultracentrifugation may be carried out by a standard process. The vector used may be a plasmid; bacteriophage, or cosmid and the most preferred vector is λ phage, which may be the one commercially available.

When a probe of low specific activity and/or low signal/noise (S/N) ratio is used, a highly nutrient medium such as SuperBroth (TM) containing casamino acids at a high concentration is used for the formation of colony or phage plaque. When E. coli is used for the host, use of strains, LE392 or JM is preferable. The non-limited filter used for the hybridization may preferably a nitrocellulose filter such as BA85 manufactured by S & S Inc.

Insertion of the DNA of a certain size into the vector may lead to unstability of the vector, and hence, insufficient signal intensity. In such a case, one plate may be blotted to, for example, three filters, and plaque selection may be carried out by observing the signal intensity of each spot in three different intensity levels.

To confirm the tissue-specific expression of the cloned gene in the mammary gland, a probe prepared from the tissue other than the mammary gland, for example, liver by the above-described procedure may be used for the contrast.

To confirm the timing-specific expression of the cloned gene in the mammary gland, a probe prepared from the mammary gland in a period other than the lactation period, for example, the mammary gland of sexually mature virgin animal by the above-described procedure may be used for the contrast.

The cloned mammary gland-specific genes may generally contain known milk protein genes such as casein protein genes, for example, α, β, γ, δ, and ε casein protein genes Japanese Patent Application Laid-Open No. 63(1988)-309192) and whey protein genes (see Japanese Patent Application Laid-Open No. 63(1988)-291), for example, WAP, α-lactoalubmin, and β-lactoalubmin (see Japanese Patent Application Laid-Open No. 3(1991)-505674), although the type of the milk protein genes present may differ by the species of the animal. Differentiation of such genes may be carried out by northern hybridization, or a hybridization carried out according to a standard procedure using an oligomer DNA probe prepared by referring to the nucleotide sequence of the particular gene. Alternatively, the differentiation of the genes may be carried out by determining the sequence of a part of the cloned DNA. In particular, mRNA of β-casein has a size somewhat similar to the mRNA of mC26 protein gene, and therefore, it is preferable to confirm the result of the differentiation by determining the nucleotide sequence.

(2) Determination of the structural gene

The resulting mC26 protein gene is evaluated by the procedure as described below to identify the expression regulatory region and the region of the structural gene.

The cloned DNA is fully or partly digested with various restriction enzymes to prepare a restriction enzyme map. The digestion products are respectively divided into three portions, and simultaneously electrophoresed on three gels, respectively. The fragments in each gel are transferred onto three filters by Southern-blotting. The three probes used for the screening of the clone are respectively reacted with the three filters for Southern hybridization. By the process as described above carried out by standard procedure or by the procedure described in the present invention, the fragments including 5' end of the structural gene, exon in the intermediate region of the structural gene, and 3' end of the structural gene are respectively identified.

Next, S1 mapping is carried out by using the DNA fragments obtained by the digestion with each of the restriction enzyme, purified mRNA extracted from mammary gland, or riboprobe prepared by using the promoter of a commercially available expression vector such as pBlue-Script II (Promega Inc.) to determine the exact position of the 5' end, the intermediate exon, and the 3' end. If desired, primer extension or PCR may be simultaneously carried out for accuracy.

On the basis of the position of the structural gene determined as described above, nucleotide sequence of the chromosomal DNA is determined by a standard procedure, and the thus obtained information is used for the subsequent synthesis of the oligomer DNA containing a part of the thus determined nucleotide sequence. The oligomer DNA synthesized is then used for the primer in the primer extension or PCR carried out for the purpose of gene structure confirmation.

The sequence of SEQ ID No. 1 is a nucleotide sequence of 5394 bp starting from the EcoRI recognition site and ending at HindIII recognition site, and this nucleotide sequence includes entire length of the structural gene region for the mouse mC26 protein gene, and regulatory region DNA sequences located in the 5' upstream and in the 3' downstream sides of the structural gene region (The sequence of SEQ ID No. 1 corresponds to the sequences of FIGS. 4, 5 and 6 ligated in this order).

(3) Construction of the expression vector

First, the EcoRI fragment including the mC26 prepared by the procedure as described above is inserted in the EcoRI cleavage site of an appropriate vector. The DNA in the vector is amplified in an appropriate host, and then recovered. The vector used is not limited to any particular type.

As shown in FIG. 5, sequences of SEQ ID No. 1 the mC26 structural gene comprises first to fourth exons, and first to third introns. Since the first exon is estimated to be involved in the protein secretion, and the introns are estimated to be involved in the splicing, it is preferable to insert the exogenous gene at a suitable site in the region of the mC26 structural gene after removing/leaving the appropriate introns and/or exon within the mC26 structural gene in consideration of the type of the exogenous gene inserted and ease in the preparation of the recombinant DNA.

Next, the process where an appropriate region in the mC26 structural gene is cleaved for removal (a process for convenient construction of the expression vector: Construction process A); and the process where the mC26 structural region from the transcription initiation site or first exon to the transcription termination site is removed (Construction procedure B) are described.

Construction process A (i) Preparation of restriction enzyme fragment

The DNA amplified in the above-described process is digested with the restriction enzyme that cleaves the transcription initiation site or the end of the first exon (hereinafter referred to as enzyme A1) and the restriction enzyme that cleaves site near the transcription termination site (hereinafter referred to as enzyme A2). In the meanwhile insert DNA fragment containing the gene to be produced in the mammary gland is prepared by the same procedure (enzymes A3 and A4).

When the enzymes A1 and A2 and the enzymes A3 and A4 are respectively the same, and the fragments produced have non-blunt ends, the DNA fragments of the vector and the insert may be ligated with no further treatment by using a DNA ligase, and the ligated DNA fragments is recovered as a circular DNA.

When the enzymes A1 and A2 are respectively different from the enzymes A3 and A4, and the fragments produced have blunt ends, either the synthetic linker method or the blunt-end method as described below is used for the smooth ligation of the vector and the insert.

(ii) Appropriate restriction enzymes

Non-limiting exemplary restriction enzymes appropriate for the use in the above (i) are shown below.

Enzyme A1 (the restriction enzyme that cleaves the site near the 5' end of the transcription initiation site or the 3' end of the first exon of the mC26 gene):

Group 1: GsuI, BsmI, ApyI, EcoRII, BstNI, MvaI, ScrFI, BsaJI;

Group 2: AluI;

Group 3: BsrI, XmnI, MboII;

Group 4: ApyI, EcoRII, BstNI, MvaI, ScrFI;

Group 5: Alw44I, ApaLI, Bsp1286I, SduI, HgiAI, DdeI, BsmAI.

Enzyme A2 (the restriction enzyme that cleaves the site near the 3' end of the transcription termination site of the mC26 gene):

Group 1: DdeI, BslI;

Group 2: BcnI, CauII, NciI, ScrFI;

Group 3: BsaJI, BcnI, CauII, NciI, ScrFI;

Group 4: XbaI.

(iii) Synthetic linker method

Synthetic DNAs, namely, linker DNAs are designed so that corresponding ends of the vector DNA and the insert DNA would become cohesive to one another after covalent bonding of the synthetic linker DNAs to the corresponding ends of the DNA. In the designing of the synthetic linker DNAs, the type of the restriction enzyme recognition sites present in the vector DNA and the insert DNA are taken into consideration.

The type of the synthetic linker DNAs actually used in the process, and the conditions of the covalent bonding process may vary depending on the nucleotide sequence of the gene to be inserted. In most cases, however, commercially available synthetic linker DNAs can be used. Alternatively, synthetic linker DNAs of desired sequence may be designed and synthesized by standard procedure.

The thus prepared DNA fragments are ligated by using a DNA ligase. By designing the synthetic linker DNAs so that the double-stranded DNA region resulting from the ligation of the cohesive ends would constitute a recognition site for the restriction enzyme, it would be possible to enable an accurate cleavage of the DNA at the same site. All of the above-described steps may be carried out by standard procedure.

(iv) Blunt end method

The blunt end method is used when the insert DNA has blunt-ended restriction enzyme cleavage ends, or when the insert DNA has restriction enzyme cleavage ends each having 5' or 3' protruding end and are incapable of undergoing direct ligation with the cleavage ends of the vector DNA. In such a case, the protruding single strand is cleaved by treating the fragment with an enzyme. The enzyme employed in such a case for the cleavage may be the one used for specific cleavage of single-stranded DNA such as S1 nuclease or P1 nuclease. It is alternatively possible to synthesize a strand complimentary with the protruding single strand by using E. coli DNA polymerase I. The resulting blunt-ended DNA fragments may be ligated by using a DNA ligase. The most commonly used DNA ligase is the ligase derived from T4 bacteriophage. All of the above-described steps may be carried out by a standard procedure, and the enzymes and the like that are used in the above-described steps are commercially available.

Construction process B

The process is described wherein the region of the mC26 structural gene from the transcription initiation site to the transcription termination site, or from the end of the first exon to the transcription termination site is accurately cleaved for removal, and the DNA of the desired gene in the form of an insert fragment is inserted therefor.

An exonuclease is reacted with the vector DNA for the mC26 gene prepared by the procedure described in the above-described Construction process A under mild conditions, and the reaction is terminated at a regular time interval to collect a series of DNA preparations. The DNA preparations were examined for their length by digestion with restriction enzymes shown in FIG. 3 to thereby confirm the formation of the DNA of the desired length.

Once the vector DNA is obtained, short DNA fragments designed for constitution of the restriction enzyme recognition site are then added to the ends of the vector DNA as described in the section of the (iii) synthetic linker method, above. The short DNA fragments may be designed so that the added short DNA fragments would be removed simultaneously with the cleavage by the restriction enzyme. For such purpose, use of a restriction enzyme such as EcoRV or PvuII that would result in the formation of the blunt ends is preferable.

To the mC26 gene vector prepared as described above, the DNA fragment of the desired gene is ligated as an insert. Either of the synthetic linker method and blunt end method described in the section of Construction process A, above, may be used for this process. Use of the blunt end method is more preferable when an accurate designing of the protein to be expressed is required.

(4) Isolation of the DNA fragment encoding the bone inducing protein (BIP)

The cDNA clone for the bone inducing protein is preferably designed such that its opposite ends are capable of being cleaved by the restriction enzyme EcoRV in one step. The thus prepared cDNA clone is then inserted into the above-described DNA vector of mC26 gene by the above-described blunt end method. For simplification of the vector construction, it is preferable to design the nucleotide sequence of the ends of the vector to which the insert is ligated such that the sites should constitute recognition sites for the restriction enzyme described as enzymes A1 and A2 in the section of Construction process A, above.

The thus prepared DNA can, be used with no further processing for the production of the gene-introduced animal. If desired, a nucleotide sequence capable of amplifying as a plasmid or temperate phage in a microorganism such as E. coli may be incorporated in the vector to enable convenient amplification and recovery of the vector in E. coli or the like by a standard procedure.

(5) Production of gene-intoduced animal

The recombinant DNA inserted in the above-described expression vector is digested with the restriction enzyme, and the DNA from expression vector such as the one from E. coli that has been used for the amplification in the prokaryotic cell is separated from the DNA of eukaryotic origin comprising the DNA of mC26 gene and the DNA of the gene to be expressed. The restriction enzyme employed is not limited to any particular type. The process, however, can be simplified by designing the plasmid and the insert such that the ligation site between the plasmid region and the 5' upstream end and the 3' downstream end of the structural gene region of the mC26 gene would become sites for recognition/cleavage by the restriction enzyme EcoRI, and using EcoRI for the cleavage.

The DNA fragments cleaved by the restriction enzyme is separated by agarose gel electrophoresis into separate bands, and the part of the agarose gel containing the band of the DNA of the gene to be expressed is cut out to extract and recover the DNA.

The thus isolated/purified DNA of eukaryotic origin is microinjected into male pronucleus of fertilized embryo with a glass pipette. The embryo is implanted in the womb of pseudo-pregnant animal (surrogate mother) after the cultivation of the embryo for a predetermined period of time or immediately after the microinjection. The process can be carried out by standard method. [See New Lessons of Experiments in Biochemistry 19, Animal Experiments (in Japanese), 1991; Gordon and Ruddle, Methods in Enzymology, 101, 411–442, 1983; Ziomek and Johnson, Cell 21, 935–942, 1980; Gordon et al., Proc. Natl. Acad. Sci., USA 77: 7380–7384, 1980; Gordon and Ruddle, Science 214, 1244–1246, 1981; Hogan et al., Manual for Mouse Embryo Manupilation (in Japanese), Kindai Shuppan.] The animal employed is not limited to any particular species. Exemplary animal employed is mouse, and use of CD-1 mouse is preferable.

The method of pseudo-pregnant animal production is zootechnologically established, and a suitable method may be selected in accordance with the animal species employed. Pseudo-pregnancy of rodents such as mouse, rat and rabbit can be easily induced by stimulating their vagina. Pseudo-pregnancy of ruminants such as cow, goat, and sheep, and horse, dog, and cat may be induced by administration of hormone reagent. If desired, hyper-ovulation may be induced by administeration of an adequate hormone reagent to the animal to increase the number of collected eggs. [See "Lectures on Experimental Biology 1: Preparation of Biological Materials (In Japanese)", Egami, N. et al. eds., Maruzen Shuppan, 1982.]

To differentiate the transgenic animal having the recombinant gene introduced therein from the animals born from the surrogate mother animal, genomic DNA extracted from a part of the body tissue of the new born animals is analyzed.

The most typical procedure for such analysis is Southern hybridization of the genomic DNA using the recombinant DNA introduced for the probe. Alternatively, such analysis may be conducted for a minute amount of the DNA by PCR wherein a synthetic DNA designed on the basis of the nucleotide sequence of the recombinant DNA is used for the primer. The above-mentioned procedures may be carried out by a standard method (See DiTullio et al., supra). The body tissue of the new born animal used for the sample may be tip of the tail in the case of mouse and rat, and earlobe in the cases of middle or large-sized animals. Mucous membrane in mouth may be also used for the sample.

Production of the exogeous gene product may be confirmed by such non-limiting means as Western blotting.

Transgenic animals are expected to have self-reproducing ability. Therefore, the procedure as described above is no longer needed once the desired trangenic animal is obtained, and the transgenic animal can be reproduced by raising the thus obtained trangenic animal, and crossbreeding the trangenic animal with another trangenic animal or non-trangenic animal to thereby produce progeny equivalent to the parent trangenic animals or that are hybrid trangenic animals.

The process of the present invention as described above has the merits as described below.

(1) Mammary gland is a tissue quite suitable for mass-production of a recombinant substance.

Mammary gland is inherently an organ capable of producing proteins and other substances in a large quantity, and use of the mammary gland is advantageous in view of availability of various domestic animals such as cow and goat that have been selectively improved for increase in the quantity of milk constituents secreted.

It should also be noted that the mammary gland is an exocirine secretory gland, and the secreted product can be recovered instantaneously by milking. Therefore, adverse effects such as aggregation of the product substance by excessive accumulation in cells of the animal, and inflammation induced by the aggregated mass can be minimized.

In addition, milk is exclusively produced in mammary gland, and there is no need to take tissue specificity into consideration. Even when the product substance is a naturally occurring substance produced in the animal body, excessive production of the substance, or production of the substance in a different tissue frequently results in the disease of the animal. Therefore secretion of the target product in the milk should minimize adverse effects on the body. Due to the tissue specificity, the target product is exclusively secreted by the mammary gland into the milk by simply introducing the recombinant gene including the expression regulatory region of the milk protein gene into the fertilized embryo.

Production of the milk in a substantial scale takes place in the mammary gland in a timing-specific manner, namely, only after the pregnancy and delivery. In other words, milk is not produced during the growh period, and normal growth of the animal would not be inhibited by the production of the target product since no milk secretion takes place during the growth period. Milk secretion of the child or adult transgenic animal, however, can be artificially initiated and maintained by inducing the milk protein production by administeration of an adequate hormone reagent. Such an artificial controllability of the milk secretion may be utilized for creation of a transgenic animal in which the recombinant gene is switched on/off at a desired timing as in the case of metallothionein gene. The thus produced animal may be used as an experimental model animal.

(2) An andvantageous production of the exogenous gene of mammal origin is enabled by the use of protein production mechanism of the mammal cell.

Addition of sugar chain to a protein, complicated modification by bonding of phosphate group or sulfur, formation of disulfide bond and the like occur in manners specific to mammals, and as a result, a protein of mammal origin with its inherent biological activity is rarely produced in bacteria such as *E. coli* . Animal cell cultures are often used for the obviation of such problem. Such use of the animal cell culture has so far been rather unsuccessful and unreliable in spite of the cost and labor required.

(3) Transgenic animals are self-reprodicible, and renewal and scale-up of the production system is easy and less costly.

Transgenic animals may be crossbred to produce progeny that are equivalent to the parent transgenic animals or that are hybrid. The process of self-reproduction requires no artificial manipulation such as genetic engineering manipulation that has been necessary for establishing the first generation transgenic animal. Therefore, production installation can be readily expanded with no significant cost, which is a merit unexpectable for a cell culture plant or chemical factory.

In addition, maintenance of the transgenic animals is safe and inexpensive. DNA replication mechanism of a microorganism such as *E. coli* is less primitive than higher animals, and the DNA produced is of lower purity. Therefore, it is difficult to maintain the properties of the cell culture at a constant level, and technology of high level is actually required in brewery for maintaining the product quality. It is also difficult to maintain a cell culture having a recombinant DNA introduced therein in a condition capable of expressing the gene for a prolonged period. In contrast, individuals of higher animals are stable, and the productivity continues for about 10 years in the case of cow. The milk productivity of cow is know to increase with the number of gestation, and milk of constant quality is economically produced for about 10 years. Similar results are expectable for the transgenic animals.

Individuals of higher animals are also provided with body protection mechanisms including the immune system, and therefore, installation for providing aseptic environment as required in the case of microorganism or animal cell culture is no longer requried. In addition, use of the higher animal is quite advantageous in view of preventing the biohazard since such production system does not involve any risk of invasion by infiltration into the human body.

The Examples of the present invention are described below by way of illustration and not by way of limitation.

In the Examples presented below, a bone inducing protein gene (a hamster-human fusion gene, haBIP) is used for the exogenous gene. Those skilled in the art will readily appreciate that the present invention is not limited to such gene and use of other exogenous gene are also allowable.

All of the expression vectors described below can amplify in microorganisms, and the vectors are not limited to the *E. coli* vectors used in the Examples presented below. The expression vector may be amplified by standard methods in the art described in, for example, Molecular Cloning and Basic Methods in Molecular Biology, supra.

EXAMPLES

Example 1

Isolation of mC26 structural gene and the expression regulatory region of the mC26 gene (i) Preparation of Probe Entire mRNA was isolated as poly(A) RNA fraction using mouse mammary gland at peak lactation (at day 10 to 12) in accordance with the standard method (Satow et al., J. Biochem. 99, 1639–1643, 1986). 10 μg of the entire mRNA was labeled with $^{32}$p by the labeling kit of Amersham or NEN using oligo(dT) primer (Biotech International/Cosmo-bio) and random hexamer (Biotech International).

For labeling the cap of the mRNA, oligo(dT) cellulose column (Bethesda Research Inc., USA/Cosmo-bio) was used in accordance with the standard method (Mizumoto and Lipmann, Proc. Natl. Acad. Sci., USA, 76, 4961, 1979) to purify the mRNA as poly(A)RNA fraction, and the purified mRNA was labeled with guanylyl transpherase (Bethesda Research Inc.) of vaccinia virus. The labeled mRNA with no further treatment and the partially digested labeled mRNA (prepared by treating the labeled mRNA with 10 to 100 ng/ml of RNaseA (Sigma, USA) at 37° C. for 1 minute and terminating the reaction with an equal volume of hormamide) were confirmed for their sizes by electrophoresis through 6% acrylamide gel containing urine at 6M to 8M).

(ii) Preparation of Library

Genomic DNA library (Clontech) of Balb/c mouse was partially or entirely digested with the restriction enzyme EcoRI. The partial digestion product was ligated with λCharon4A, and the entire digestion product was ligated with pSP64 (Promega Biotech, USA) to prepare the library.

cDNA and genomic DNA libraries inserted in a λ phage vector such as λgt10, λgt11, EMBL3, or λCharon4A are commercially available for such animal species as cow, chicken, dog, goat, guinea pig, hamster, human, kangaroo, monkey, mouse, dove, pig, rabbit, rat, sheep (Clontech/TOYOBO). Those skilled in the art would also be readily capable of preparing equivalent libraries by the combined use of pSP64 (Promega Biotech, USA) and commercially available genomic DNA.

(iii) Screening of Positive Clones

The thus prepared library was screened using the probe prepared in the above (i).

Figure 2:
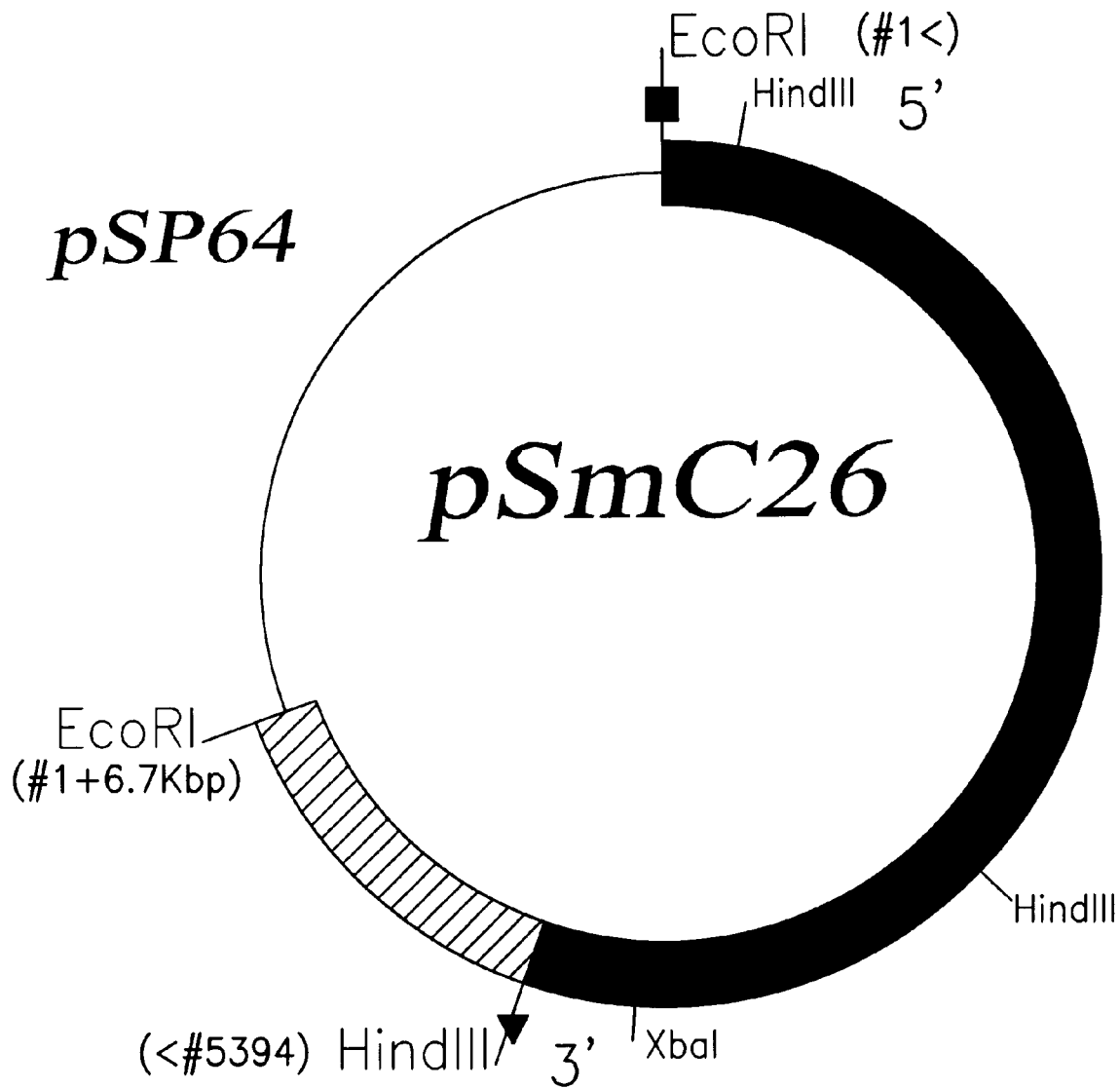
FIG. 2 is a restriction enzyme map of pSmC26. The region shown by the frame other than the EcoRI-EcoRI region derived from pSP64 corresponds to the EcoRI fragment of about 6.7 kb, namely, the region shown by the frame from the EcoRI (#<) to the EcoRI (#1+6.7 kbp) in FIG. 1. The indications of 5' and 3' are those for the mC26 structural gene.

As a result of such screening, λMC26 and pSmC26 were identified from λCharon4A and pSP64 libraries, respectively, as positive clones exhibiting mammary gland-specific expression. The map of the structures are shown in FIGS. 1 and 2, respectively.

Example 2

Characterization of mC26 structural gene and the expression regulatory region of the mC26 gene (i) Characterization of Positive Clone Restriction maps of λMC26 and pSmC26 clones were prepared and compared with each other. It was then revealed that λMC26 includes a fragment (EcoRI fragment) of about 12.7 kb; that pSmC26 includes a fragment (EcoRI fragment) of about 6.7 kb; and that the fragment of about 6.7 kbp is included in the fragment of about 12.7 kb. Such results are apparent from the comparison of restriction enzyme recognition sites as shown FIGS. 1 and 2.

(ii) Sequencing

Figure 3:
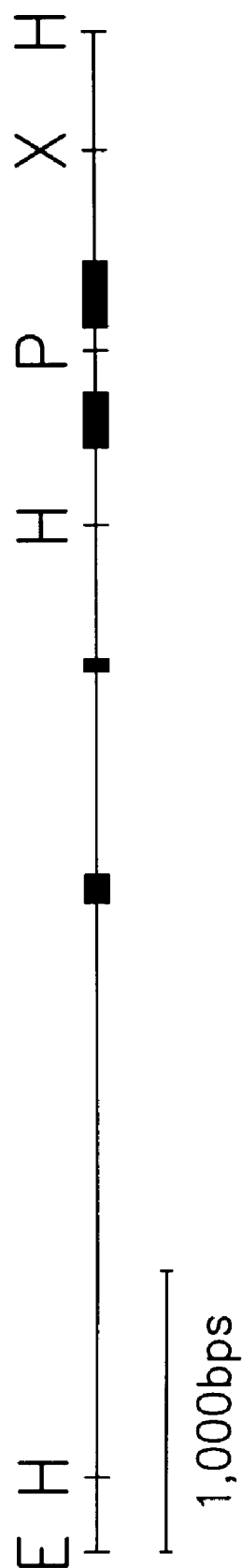
FIG. 3 is a restriction enzyme map of SEQ ID No. 1. The letter E represents the restriction enzyme EcoRI; X represents the restriction enzyme XbaI; P represents the restriction enzyme PstI; and H represents the restriction enzyme HindIII. The boxes represent exons.

The EcoRI fragment of about 6.7 kb was cut out from pSmC26 and the fragment was digested with HindIII. The resulting EcoRI-HindIII fragment of about 5.4 kb was inserted in pBlueScriptIISK+ (Promega) for subcloning. A series of deletion mutants were prepared for the subclone by using a deletion kit (TaKaRa). The restriction map for the fragment of about 5.4 kb is shown in FIG. 3. The deletion mutants were sequenced by dideoxy method (Sanger, F. et al., Proc. Natl. Acad. Sci., USA, 74, 5463, 1977) with a DNA sequencer (Model 373A, ABI; Model A.L.F., Pharmacia). The nucleotide sequence determined is SEQ ID No. 1.

The sequence of SEQ ID No. 1 includes the structural gene region starting from AGC (nucleotide numbers 2305 to 2307) and terminating at CCT (nucleotide numbers 4622 to 4624) (FIG. 5).

As shown in FIG. 5 sequences of SEQ ID No. 1, the mC26 structural gene includes introns 1, 2 and 3, which are estimated to be involved in splicing. Upon expression of the exogenous gene, it would be preferable to include such sequences in the expression cassette. As will be demonstrated in the following examples, some exogenous genes do require such sequences for their expression. In determining whether such sequences should be included in the expression cassette, complexity of ligation of such sequences should also be taken into consideration.

The nucleotide sequences in the upstream and the downstream of the structural gene has no homology with the known casein gene. The region that is not disclosed in Dowbenko, supra, namely, the region where GAA triplets are continuously repeated (hereinafter referred to as MboII repeats), is estimated to be equivalent with the expression regulatory sequence which are the so called triple repeats. This region (FIG. 4 sequences of SEQ ID No. 1, the underscored sequence) is highly susceptible of being involved in the regulation of the expression. MboII estimated to function as an expression regulating enhancer. MboII repeats as shown in FIG. 4 sequences of SEQ ID No. 1 play an important role in the expression of the mC26 gene.

The nucleotide sequence of SEQ ID No. 1 was readily separated from λMC26 and pSmC26 clones as a DNA fragment that is terminated at one end by the EcoRI recognition site and on the other end by HindIII recognition site, and the sequence was used for the expression cassette in the subsequent procedure.

Example 3

Preparation of Transgenic Animal Expressing mouse bone inducing protein

Of the fragment of about 6.7 kb in pSmC26 isolated in Example 1, a DNA fragment of 5394 bp whose sequence had been determined was used for the expression cassette to prepare the recombinant DNA having an exogenous gene ligated in the region of the mC26 structural gene. The procedure is summarized below.

(i) Preparation of Recombinant DNA

Figure 7:
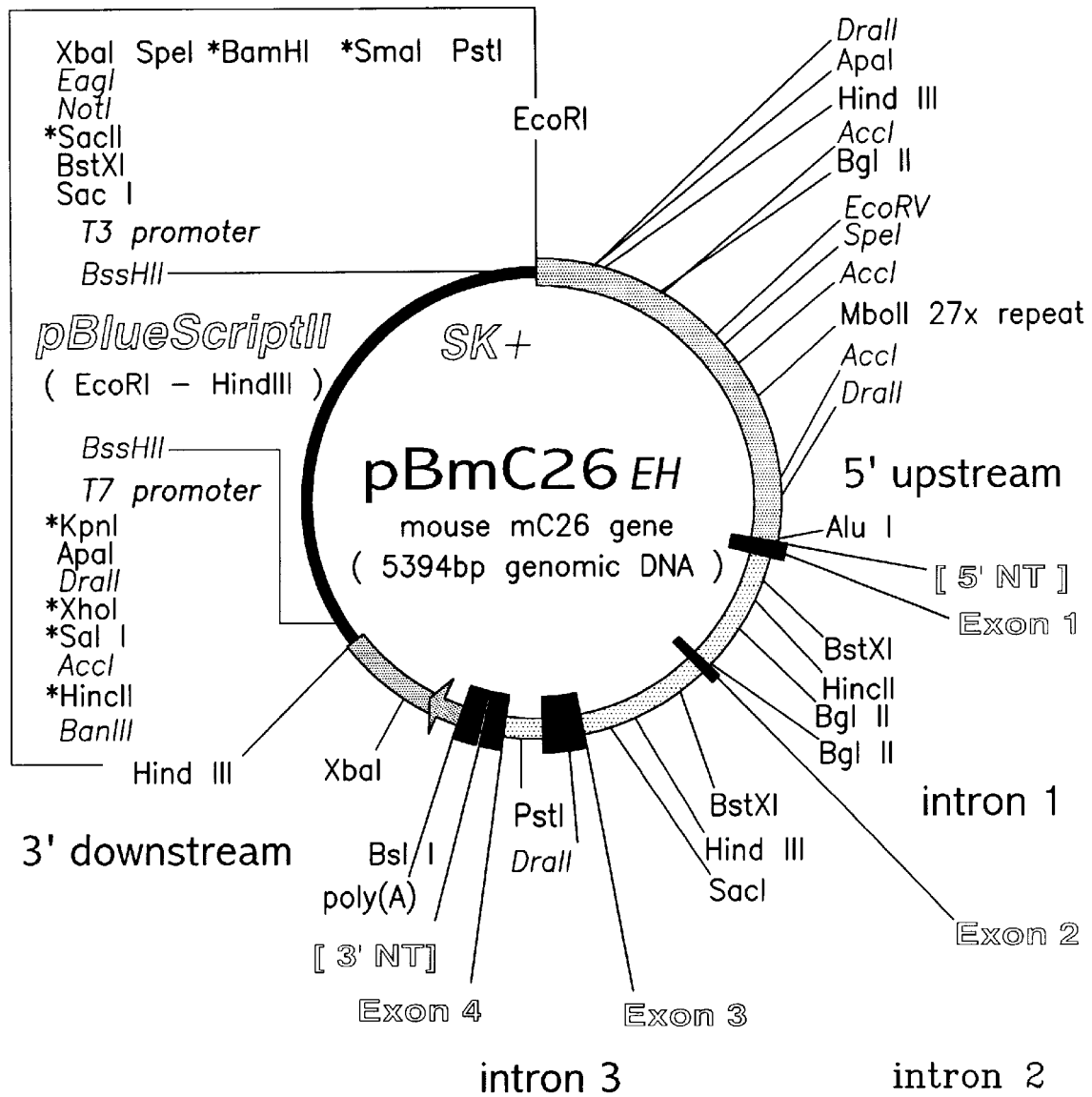
FIG. 7 is a restriction enzyme map of pBmC26EH. The region shown by the solid line is derived from pBlueScriptII SK+. The region other than the region shown by the solid line is the EcoRI-HindIII fragment of SEQ ID No. 1, which is a DNA fragment of about 5394 bp.

The EcoRI fragment of about 6.7 kb was recovered from pSmC26, and the fragment was partially digested with HindIII. A DNA fragment of 5394 bp was then recovered by gel electrophoresis. The thus recovered fragment was ligated to an EcoRI/HindIII double digestion product of pBlueScriptSK+ to prepare pBmC26EH. The map of pBmC26EH is shown in FIG. 7.

The exogenous gene used was bone inducing protein (BIP) gene and it was a hamster-human fusion gene whose nucleotide sequence is SEQ ID No. 2.

The fusion gene was produced by the procedure as described below from the RNA (10 μg) extracted from Baby Hamster kidney (BHK) cell line derived from hamster in accordance with a standard method (Thionianate guanidine method; Sambrook et al., Molecular Cloning, supra) by using the DNAs which are respectively parts of the human bone inducing protein (BIP) gene and having the sequences of GACGAGAAGACGATGCAGA (SEQ ID No. 7) and GCACAGGTGTCCACGGACA (SEQ ID No. 8)

for the 5' primer and the 3' (reverse strand) primer; and reverse transcriptase RAV-2 (TaKaRa) and rTthDNA polymerase (Perkin Elmer/TaKaRa) in an RT-PCR reaction carried out in accordance with the procedure described in the manual of Perkin Elmer Cetus DNA Thermal Cycler 480 using the buffer attached therewith to produce a double strand DNA complimentary to the hamster BIP. After confirming the production of the double strand DNA by electrophoresis (FIG. 8, lanes 3 to 5), the double strand DNA was recovered from the gel, and inserted into the EcoRV cleavage site of the pBlueScriptII vector to amplify the DNA. The DNA was then sequenced by an automatic sequencer (ALF, Pharmacia). By the procedure as described above, there was obtained a human-hamster fusion gene DNA comprising the human BIP DNAs (SEQ ID Nos. 7 and 8) ligated to the region of the hamster BIP gene that is homologous to the human gene.

A recombinant DNA was prepared by ligating the thus obtained DNA to the DNA of SEQ ID No. 1 in pBmC26EH from which the region of from 2305th nucleotide to 4624th nucleotide has been deleted by using T4 DNA ligase (TaKaRa). The resulting recombinant DNA was transfected in *E. coli* JM 109 strain to amplify the recombinant DNA. The amplified recombinant DNA was sequenced for confirmation, and digested with the restriction enzyme BssHII (TaKaRa) to produce a linear DNA. The linear DNA was subjected to agarose gel electrophoresis to separately recover the DNA region of pBlueScriptII origin and the region of the mC26 expression cassette having haBIP inserted therein. Solutions of the resulting DNA at 1 to 5 µg/ml were used in the Examples as described below.

(ii) Collection of Fertilized Egg

Mice were examined for their actual estrus cycle by taking the fact that typical estrus cycle of mouse is four days into consideration. The estrus cycle examination was carried out by washing the vagina of the female mouse with water using a glass pipette and conducting cell diagnosis (smear check). Mice were divided into groups of mice in synchronized estrus cycle, and the mice were bred in synchronized estrus cycle groups. Female mice were checked for the formation of vaginal plug on the next morning after the mating with the male mouse to obtain pregnant mice. When the population size of the female mice is small, gonadtropin is intraperitneally injected to female mice to thereby induce hyper-ovulation. Ketamine hydrocloride or pentoobarbital that has been diluted to 50-folds was intraperitoneally injected for introducing anesthesia, and operation was conducted under ether anesthesia to collect the oocyte that is moving through the oviduct or cervical corn.

The mouse used was CD-1 from Charles River.

(iii) Injection of DNA into Fertilized Egg pBmC26EH prepared in the above (i) was amplified in *E. coli* JM109, and the plasmid was cleaved at the recognition sites of the restriction enzymes EcoRI and KpnI for linearlization. The thus linearlized DNA was injected into pronucleus of the fertilized egg by dissolving the DNA to a concentration of 1 to 5 µg/ml and injecting the solution to the fertilized egg. A silicone tube catheter was inserted into the abdominal opening of oviduct of a female mouse in pseudopregnancy induced by cervical stimuli or the foster mother (recipient female) selected from the synchronized estrus cycle groups, and the engineered embryo was inserted into the oviduct through the silicone tube catheter to induce pregnancy.

One-hour survival rate of oocyte after the microinjection was 52%.

20 micro-injected eggs prepared by the above-described procedure were introduced into one recipient female, and pregnancy was induced in 40 recipient females, and as a result, 54 baby mice were obtained.

Of the 54 baby mice obtained, 7 mice (13%) were determined to be transgenic by means of DNA diagnosis.

(iv) DNA diagnosis

DNA was obtained from mouth mucous membrane cell or leukocyte culture of the transgenic mouse by a normal method, and the resulting DNA was subjected to a DNA diagnosis by using a PCR kit (Perkin Elmer) in accordance with the manufacture's manual. The results are shown in FIG. 8.

Figure 8:
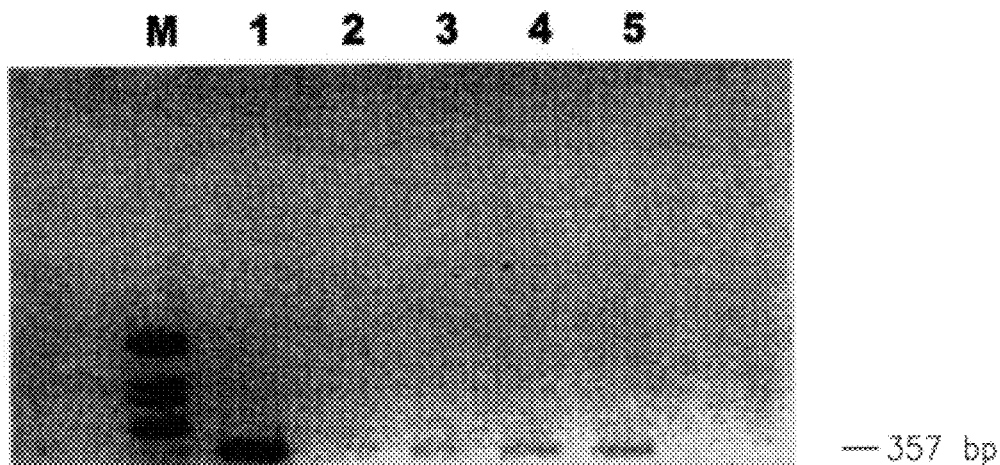
FIG. 8 shows the results of DNA diagnosis by PCR. After the PCR, the product was subjected to electrophoresis on 2% agarose gel, and staining with ethidium bromide. M shows the molecular weight marker. Lane 1 shows the recombinant animal cell (human-hamster recombinant BIP), lane 2 shows Namalwa cell (negative control), lane 3 shows BHK cell line 1; lane 4 shows BHK cell line 2, and lane 5 shows BHK cell line 3.

FIG. 8 shows the results of the confirmation by RT-PCR of the expression of the mRNA of haBIP, a human-hamster fusion gene, for 10 µg of RNAs respectively extracted from cell line cultures and the recombinant animal cell. Lanes 4, 5 and 6 are the results of the RT-PCR for RNAs extracted from BHK cells from hamster; lane 2 is the results for RNA of the Namalwa cell, a cell line from human; and lane 1 is the results for RNA extracted from the recombinant animal cell. The 5' and 3' primers are those prepared by synthesizing oligomer DNAs in accordance with the sequence of the region of the structural gene in the human BIP gene DNA, and the PCR reaction products will have identical DNA sequence. FIG. 8 shows the results of the electrophoresis on 2% agarose gel of the PCR reaction products after staining with ethidium bromide. The agarose of each band was cut out and dissolved in NaI, and the DNA was recovered by adsorption onto glass powder to determine the full nucleotide sequence of the DNA. The DNAs recovered were confirmed to have the same nucleotide sequence.

I claim:

1. A DNA comprising the nucleotide sequence of SEQ ID No. 1 wherein an exogenous gene coding region is inserted at one position in the region of nucleotides 2305 to 4624.

2. The DNA according to claim 1 wherein at least one of exons 1 to 4 and introns 1 to 3 of the nucleotide sequence of SEQ ID No. 1, as depicted in FIG. 5, is deleted.

3. The DNA according to claim 1 wherein said exogeneous gene is the gene encoding bone inducing protein (BIP).

4. An expression vector containing the DNA according to claim 1.

5. The expression vector according to claim 4 which is replicable in *E. coli*.

* * * * *